(12) United States Patent
Naughton

(10) Patent No.: US 6,186,971 B1
(45) Date of Patent: Feb. 13, 2001

(54) SWAB DISPENSER WITH INTEGRAL FLUID RESERVOIR

(76) Inventor: John G. Naughton, 174 Linden Dr., Cohasset, MA (US) 02025

( * ) Notice: Under 35 U.S.C. 154(b), the term of this patent shall be extended for 0 days.

(21) Appl. No.: 09/576,669

(22) Filed: May 23, 2000

(51) Int. Cl.[7] .......................... A61M 35/00; B65D 83/10; A61B 17/06; A46B 11/00

(52) U.S. Cl. .................. 604/2; 206/210; 206/362; 206/363; 206/438; 401/118; 401/125; 401/129

(58) Field of Search ................ 604/1–3; 206/210, 206/361, 362, 362.3, 363, 438, 63.5, 828; 401/88, 118, 123, 125, 129; 606/162

(56) References Cited

U.S. PATENT DOCUMENTS

| | | |
|---|---|---|
| 3,146,806 | 9/1964 | Ginsburg . |
| 3,881,868 * | 5/1975 | Duke ..................................... 206/438 |
| 4,190,153 * | 2/1980 | Olsen ................................... 206/362 |
| 4,446,965 | 5/1984 | Montiel . |
| 4,747,719 | 5/1988 | Parkin . |
| 5,016,651 | 5/1991 | Stalcup et al. . |
| 5,112,297 * | 5/1992 | Stalcup et al. ............................ 604/1 |
| 5,131,536 * | 7/1992 | Wu ........................................ 206/362 |
| 5,330,056 * | 7/1994 | Rocha ................................... 206/362 |
| 5,378,226 | 1/1995 | Hanifl et al. . |
| 5,709,866 | 1/1998 | Booras et al. . |
| 5,947,986 * | 9/1999 | Lewis ....................................... 604/1 |

* cited by examiner

Primary Examiner—Dennis Ruhl
(74) Attorney, Agent, or Firm—Morse, Altman & Martin

(57) ABSTRACT

A swab dispenser comprising a bin adapted to store swabs, a fluid reservoir, and optionally, a cover. The bin may be compartmentalized. The reservoir ceiling has a depression in its outer surface and an aperture at the low point of the depression. A membrane covers the aperture. The membrane has at least two intersecting slits that allows a swab to be inserted into the reservoir by temporarily deforming the membrane. Preferably, the slits extend completely across the aperture. Preferably, the floor of the reservoir is concave with the low point directly below the aperture.

13 Claims, 1 Drawing Sheet

SWAB DISPENSER WITH INTEGRAL FLUID RESERVOIR

BACKGROUND OF THE INVENTION

1. Field of the Invention

The present invention relates to arts and crafts and health and beauty products, more particularly, to a device for storing swabs and a wetting fluid.

2. The Prior Art

Cotton swabs are handy tools for applying fluids to small areas, for example, rubbing alcohol, nail polish remover, or paint. The swabs are stored in one container and the application fluid is stored in a separate covered container. The user removes a swab from its container, removes the cap from the fluid container, wets the swab by dipping it into the fluid, and then replaces the cap. In most cases, the fluid container is substantially deeper than the length of the swab, so the container must be tilted to wet the swab, requiring two hands. Having to manipulate the swab, cap, and fluid container can be awkward and prone to accidents, particularly when putting the cap back on the fluid container while holding a wet swab. There is also the convenience factor of having to deal with two containers which may or may not be stored together.

Several solutions to the problem have been posed. For example, in U.S. Pat. No. 3,146,806, the fluid container is fitted with a stopper through which a swab can be pushed for wetting. Although this device substantially reduces the risk of accidental spillage, it does not alleviate the inconvenience of having two separate containers.

A different solution is suggested by U.S. Pat. No. 4,747,719. In this patent, the fluid is stored in hollow in the handle of the swab. When wetting is desired, the user pushes the swab onto a pin to prick a hole in the hollow, allowing the fluid to escape and wet the swab. The shortcomings of this device are that it is a one-use-only device that is relatively complicated and expensive to produce. Also, both the swab and the swab container with the pin need to be disposed of after use, no part of the device is reusable. Finally, it is not particularly cost-effective for home use.

A third solution is suggested by U.S. Pat. No. 5,378,226. In this patent, the swab is stored in a sealed bag with a smaller burst pouch that holds the fluid. The pouch is burst open while the bag is sealed, and the fluid from the pouch wets the swab within the bag. Then the bag is opened and the swab is removed. Like with the '719 patent above, this is a one-use-only device that is relatively complicated and expensive to produce. The '226 patent does disclose that there may be more than one swab in the bag. They are all wetted at the same time and must either be used or disposed of. Also like the '719 patent, all components of the device need to be disposed of after use, no part of the device is reusable. Finally, this device is not particularly convenient or cost-effective for home use.

Thus there continues to be a need for a device to safely and conveniently store swabs and wetting fluid.

SUMMARY OF THE INVENTION

An object of the present invention is to provide a swab dispenser with an integral fluid reservoir for safely and conveniently storing swabs and a wetting fluid.

Another object is to provide a swab dispenser that is cost-effective for home, commercial, industrial use.

A further object is to provide a swab dispenser that only requires one hand to remove and wet a swab.

The present invention is a swab dispenser adapted for use with a swab that has a relatively straight, rigid handle with an absorbent material attached at an end thereof. The dispenser has a storage bin for swabs and a reservoir for a wetting fluid. The storage bin is an open top compartment that is optionally separated into compartments. The swabs stand generally vertically.

The reservoir holds a fluid for wetting the swab, so the walls of the reservoir must be impervious to the fluid. The only opening to the reservoir is an aperture in the ceiling at the low point of a depression in the ceiling. The depression causes the fluid to flow down the depression surface to the aperture. The reservoir floor is concave, with the lowest point directly below the aperture so that the fluid flows to where it is most convenient for wetting the swab.

The aperture is covered by a membrane that minimizes evaporation and spillage of the fluid. The membrane has at least two intersecting slits through which the swab is pushed, causing the membrane to deform inwardly and opening a hole for the swab. The membrane is composed of a material that returns the membrane to its original shape when the swab is removed. Preferably, the slits extend across the entire aperture and the membrane. If the slits are shorter, they may tear with repeated use, increasing the size of the opening and allowing more potential evaporation and spillage.

Optionally, the swab dispenser of the present invention includes a clear cover for protecting the swabs from contamination, providing some protection against fluid spills, and further retarding evaporation.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Figure 1:
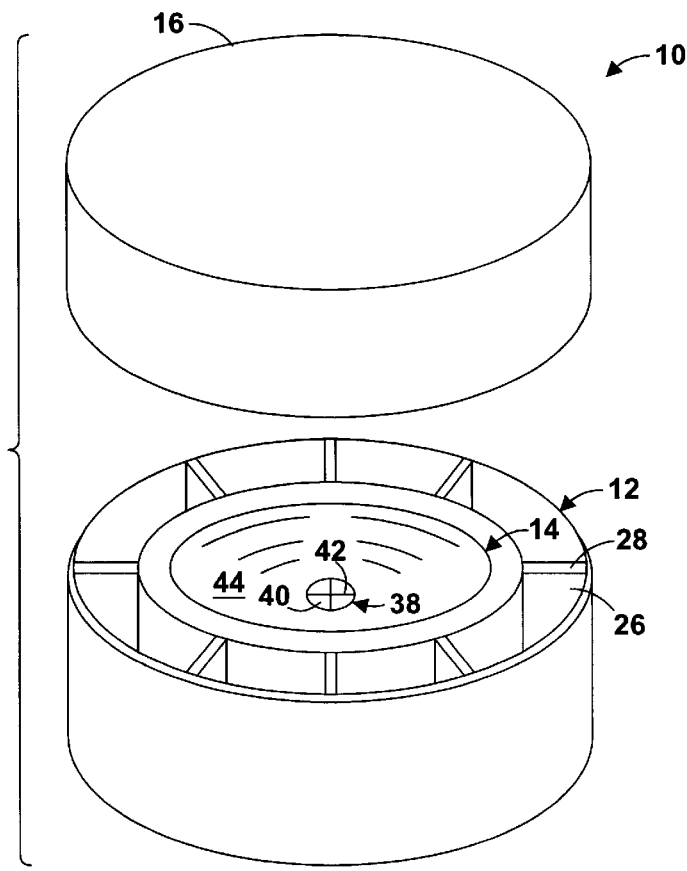
FIG. 1 is a top perspective view of the swab dispenser of the present invention.
Figure 2:
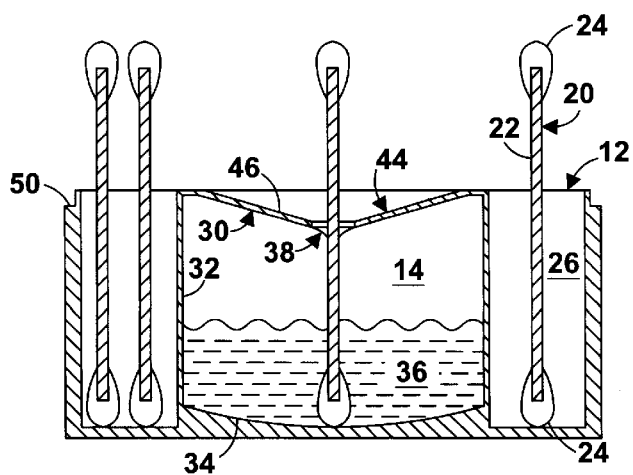
FIG. 2 is a cross-section of the swab dispenser of FIG. 1.

The swab dispenser 10 of the present invention is shown in FIGS. 1 and 2. The basic dispenser 10 has a storage bin 12 for swabs and a reservoir 14 for a wetting fluid. The present invention is intended for use with swabs 20 that have a rigid handle 22 with an absorbent material 24, typically cotton, at one or both ends.

The storage bin 12 is preferably an open top compartment where the swabs 20 stand generally vertically. Optionally, the bin 12 is separated into a set of smaller compartments 26 by walls 28. The compartments 26 provides several functions. If the compartments 26 are relatively small, the swabs remain relatively vertical when there are few swabs in the bin 12 to hold each other up. If there are few swabs in the bin 12, the swabs tend to fall over. The walls 28 provide a support to hold the swabs up. More than one compartment 26 also makes it easier to separate different types of swabs so that they do not mingle and makes them easier to locate and remove.

The reservoir 14 holds a fluid 36 for wetting the swab 20 prior to use. The fluid 36 depends upon the application and may be, for example, rubbing alcohol, nail polish remover, antiseptic solutions, detergent solutions, plastic model cement, paint, or any kind of fluid that one may wish to apply with a swab. The reservoir 14 must be composed of a material that is impervious to the fluid 36. Alternatively, the inner walls of the reservoir 14 are coated with a material that renders the walls impervious to the fluid 36.

The reservoir 14 is nearly fully enclosed, with a ceiling 30, side walls 32, and floor 34. The only opening to the reservoir 14 is an aperture 38 in the ceiling 30 through which the swab 20 is pushed for wetting. The aperture 38 is preferably round, but may have any shape. The aperture 38 is at the low point of a depression 44 in the ceiling 30. The depression 44 is sloped so that most fluid 36 will flow down the depression surface 46 to the aperture 38. The preferred range of angles of slope of the depression surface 46 depends upon the intended application of the present invention 10. The more viscous the fluid 36, the steeper the angle needs to be in order for the fluid 36 to flow down the slope.

The aperture 38 is preferably covered by a membrane 40 that retards evaporation and minimizes spillage of the fluid 36. The membrane 40 has at least two intersecting slits 42 through which the swab 20 is pushed. When there are two slits 42, they are preferably at approximately a 90° to each other, forming an X, as in FIG. 1.

Figure 3:
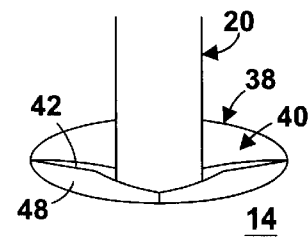
FIG. 3 is an enlarged perspective view of the membrane of FIG. 1 with a swab inserted.

As a swab 20 is pushed through the slits 42, the membrane 40 deforms inwardly, as in FIG. 3, opening a hole for the swab 42. Preferably, the opening is only large enough to allow the swab 20 to fit through easily. The smaller the opening, the less evaporation and spillage of the fluid 36 they can be.

It is also preferred that the slits 42 extend across the entire aperture 38 and the membrane 40. If the aperture 38 is round, the length of the slits 42 is the same as the diameter of the aperture 38 and membrane 40. If the slits 42 are shorter than the membrane diameter, the slits 42 may tear with repeated use, increasing the size of the opening. And because the tearing will be irregular, the edges of the tear will not match, and the opening will no longer close. With this preferred configuration, the membrane 40 will not actually be a unitary component, but will consist of four 90° sections 48 of membrane 40, each attached to the edge of the aperture 38. The present invention does contemplate that the membrane 40 may be larger than the slits 42, provided that the membrane 40 is composed of a material that resists tearing with repeated use.

As indicated above, one use of the membrane 40 is to reduce evaporation and spillage. Another possible use is to wipe excess fluid 36 from the swab 20 as it is pulled from the reservoir 14. As a swab 20 is pushed through the slits 42, the membrane sections 48 deform inwardly. As the swab 20 is pulled from the reservoir 14, the membrane sections 48 tend to deform outwardly. As the absorbent material 24 of the swab 20 passes the membrane sections 48, pressure from the membrane sections 48 against the absorbent material 24 squeezes off fluid that would most likely drip off the swab 20 prior to use.

The membrane 40 is composed of a material that is resilient so that it deforms inwardly when pushed by the swab 20, and is rigid enough so that it returns to its original state to cover the aperture 38 to retard evaporation when the swab 20 is removed. Preferably, the membrane 40 is composed of a rubber or plastic material.

Preferably, the floor 34 of the reservoir 14 is concave, with the lowest point directly below the aperture 38. With a flat floor, as the level of the fluid falls, the user typically needs to tilt the reservoir to wet the swab. The concave floor 34 of the present invention eliminates the need to tilt the reservoir 14 by using gravity to cause the remaining fluid 36 to pool at the lowest point under the aperture 38, where the fluid 36 is easiest to reach.

The figures show a circular reservoir 14 in the center of the circular bin 12. This arrangement is merely illustrative. Any arrangement of the bin 12 and reservoir 14 is contemplated by the present invention, as long as they are integrated into a single package.

The present invention contemplates that the dispenser 10 may be manufactured and sold with the reservoir 14 already filled with a fluid and/or that the reservoir 14 may be refilled from another container. The reservoir 14 would be refilled through the aperture membrane 40.

Optionally, the swab dispenser 10 of the present invention includes a cover 16. The cover 16 fits in a lip 50 on the outer wall of the integral bin/reservoir. The cover 16 provides several advantages. It protects the swabs 20 from contamination, provides some protection against fluid spills if the dispenser 10 should be knocked over or dropped, and further retards evaporation of the fluid 36. Preferably, the cover 16 is clear so that the swabs 20 are visible.

Thus it has been shown and described a swab dispenser with an integral fluid reservoir which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A swab dispenser adapted for use with a swab having a relatively straight, rigid handle with an absorbent material attached at an end thereof, said dispenser comprising:
    (a) a bin adapted to store said swabs;
    (b) a fluid reservoir having a ceiling, said ceiling having an outer surface with a depression with a low point;
    (c) an aperture in said ceiling at said low point of said depression; and
    (d) a membrane covering said aperture, said membrane having at least two intersecting slits adapted to allow said swab to be inserted through said slits into said reservoir by temporarily deforming said membrane.

2. The swab dispenser of claim 1 wherein said reservoir has a concave floor with a low point located approximately under said aperture.

3. The swab dispenser of claim 1 wherein said swab dispenser further comprises a removable cover.

4. The swab dispenser of claim 1 wherein said bin has walls dividing said bin into a plurality of compartments.

5. The swab dispenser of claim 1 wherein said bin stores said swabs approximately vertically.

6. The swab dispenser of claim 1 wherein said slits extend completely across said aperture.

7. The swab dispenser of claim 1 wherein there are two of said slits forming an approximately 90° angle to each other.

8. A swab dispenser adapted for use with a swab having a relatively straight, rigid handle with an absorbent material attached at an end thereof, said dispenser comprising:
    (a) a bin adapted to store said swabs;
    (b) a fluid reservoir having a ceiling and a floor, said ceiling having an outer surface with a depression with a low point;

(c) an aperture in said ceiling at said low point of said depression;

(d) said floor being concave with a low point located approximately under said aperture; and (e) a membrane covering said aperture, said membrane having at least two intersecting slits adapted to allow said swab to be inserted through said slits into said reservoir by temporarily deforming said membrane, said slits extending completely across said aperture.

9. The swab dispenser of claim 8 wherein said swab dispenser further comprises a removable cover.

10. The swab dispenser of claim 8 wherein said bin has walls dividing said bin into a plurality of compartments.

11. The swab dispenser of claim 8 wherein said bin stores said swabs approximately vertically.

12. The swab dispenser of claim 8 wherein there are two of said slits forming an approximately 90° angle to each other.

13. A swab dispenser adapted for use with a swab having a relatively straight, rigid handle with an absorbent material attached at an end thereof, said dispenser comprising:

(a) a bin adapted to store said swabs, said bin having walls dividing said bin into a plurality of compartments for storing said swabs approximately vertically;

(b) a fluid reservoir having a ceiling and a floor, said ceiling having an outer surface with a depression with a low point;

(c) an aperture in said ceiling at said low point of said depression;

(d) said floor being concave with a low point located approximately under said aperture;

(e) a membrane covering said aperture, said membrane having at least two intersecting slits adapted to allow said swab to be inserted through said slits into said reservoir by temporarily deforming said membrane, said slits extending completely across said aperture; and (f) a removable cover.

* * * * *